(12) United States Patent
Maier et al.

(10) Patent No.: US 7,564,546 B2
(45) Date of Patent: Jul. 21, 2009

(54) DYNAMIC IMAGING OF BIOLOGICAL CELLS AND OTHER SUBJECTS

(75) Inventors: John S. Maier, Pittsburgh, PA (US);
Patrick J. Treado, Pittsburgh, PA (US);
David Tuschel, Monroeville, PA (US);
Thomas C. Voigt, Export, PA (US)

(73) Assignee: ChemImage Corporation, Pittsburgh, PA (US)

( * ) Notice: Subject to any disclaimer, the term of this patent is extended or adjusted under 35 U.S.C. 154(b) by 99 days.

(21) Appl. No.: 10/556,038

(22) PCT Filed: Jun. 30, 2005

(86) PCT No.: PCT/US2005/023638

§ 371 (c)(1),
(2), (4) Date: Mar. 12, 2007

(87) PCT Pub. No.: WO2006/005022

PCT Pub. Date: Jan. 12, 2006

(65) Prior Publication Data

US 2007/0182959 A1    Aug. 9, 2007

(51) Int. Cl.
*G01J 3/44* (2006.01)
*G01N 21/65* (2006.01)

(52) U.S. Cl. .................................... 356/301
(58) Field of Classification Search ............. 356/301
See application file for complete search history.

(56) References Cited

U.S. PATENT DOCUMENTS

| | | |
|---|---|---|
| 5,194,912 A | 3/1993 | Batchelder et al. |
| 5,261,410 A | 11/1993 | Alfano et al. |
| 5,377,004 A | 12/1994 | Owen et al. |
| 5,442,438 A | 8/1995 | Batchelder et al. |
| 5,539,517 A | 7/1996 | Cabib et al. |
| 5,596,992 A | 1/1997 | Haaland et al. |
| 5,623,342 A | 4/1997 | Baldwin et al. |

(Continued)

FOREIGN PATENT DOCUMENTS

WO    2006091853    8/2006

OTHER PUBLICATIONS

Ling et al, Direct Raman imaging techniques for study of the subcellular distribution of a drug, Applied Optics, vol. 41, No. 28, Oct. 1, 2002, pp. 6006-6017.*

(Continued)

*Primary Examiner*—F. L Evans
(74) *Attorney, Agent, or Firm*—Morgan Lewis & Bockius LLP

(57) ABSTRACT

The invention relates to methods of dynamic chemical imaging, including methods of cellular imaging. The method comprises illuminating at least a portion of a cell with substantially monochromatic light and assessing Raman-shifted light scattered from the illuminated portion at a plurality of discrete times. The Raman-shifted light can be assessed at a plurality of Raman shift (RS) values at each of the discrete times, and the RS values can be selected to be characteristic of a pre-selected component at each of the discrete times. Multivariate analysis of Raman spectral features of the images thus obtained can yield the location and chemical identity of components in the field of view. This information can be combined or overlaid with other spectral data (e.g., a visible microscopic image) obtained from the field of view.

13 Claims, 2 Drawing Sheets

U.S. PATENT DOCUMENTS

| | | | |
|---|---|---|---|
| 5,689,333 | A | 11/1997 | Batchelder et al. |
| 5,733,739 | A | 3/1998 | Zakim et al. |
| 5,769,081 | A | 6/1998 | Alfano et al. |
| 5,891,619 | A | 4/1999 | Zakim et al. |
| 6,002,476 | A | 12/1999 | Treado |
| 6,151,522 | A | 11/2000 | Alfano et al. |
| 6,205,354 | B1 | 3/2001 | Gellermann et al. |
| 6,571,118 | B1 | 5/2003 | Utzinger et al. |
| 6,640,132 | B1 | 10/2003 | Freeman et al. |
| 6,665,556 | B1 | 12/2003 | Alfano et al. |
| 6,741,884 | B1 | 5/2004 | Freeman et al. |
| 6,937,885 | B1 | 8/2005 | Lewis et al. |
| 7,046,359 | B2 * | 5/2006 | Voigt et al. .................. 356/301 |
| 7,317,526 | B2 * | 1/2008 | Voigt et al. .................. 356/301 |
| 7,383,077 | B2 | 6/2008 | Zeng |
| 2001/0044129 | A1 * | 11/2001 | Ling et al. ..................... 435/32 |
| 2002/0007123 | A1 | 1/2002 | Balas |
| 2004/0038320 | A1 | 2/2004 | Banerjee |
| 2005/0240107 | A1 | 10/2005 | Alfano et al. |
| 2006/0013454 | A1 | 1/2006 | Flewelling et al. |
| 2006/0155195 | A1 | 7/2006 | Maier et al. |
| 2006/0250613 | A1 | 11/2006 | Demuth et al. |
| 2006/0253261 | A1 | 11/2006 | Maier et al. |
| 2006/0269972 | A1 | 11/2006 | Smith et al. |
| 2006/0281068 | A1 | 12/2006 | Maier et al. |
| 2007/0093708 | A1 | 4/2007 | Benaron et al. |

OTHER PUBLICATIONS

Chandler, W.F. et al., "Intraoperative Use of Real-time Ultrasonography in Neurosurgery", J. Neurosurg (1982) pp. 157-163, vol. 57.

Poon, W.S. et al., "Laser-Induced Fluorescence: Experimental Intraoperative Delineation of Tumor Resection Margins", J. Neurosurg (1992) pp. 679-686, vol. 76.

Hansen, D.A. et al., "Indocyanine Green (ICG) Staining and Demarcation of Tumor Margins in a Rat Glioma Model", Surgical Neurol. (1993) pp. 451-456, vol. 40.

Haglund, M.M. et al., "Enhanced Optical Imgaing of Rag Gliomas and Tumor Margins", Neurosurgery (1994) pp. 930-941, vol. 35, No. 5.

Yuan, X. et al., "Isolation of Cancer tem Cells from Adult Glioblastoma Multiforme", Oncogene (2004) pp. 9392-9400, vol. 23.

Ahmad, K., Small Subsets of Cells Initiate Brain Tumors, Lancet Oncology (2005) pp. 9, vol. 6.

Dirks, P.B., "Brain Tumor Stem Cells", Biology of Blood Marrow Transplantation (2005) pp. 12-14, vol. 11.

Bakker Schut, T.C. et al., "Real-Time Tissue Characterization on the Basis of in vivo Raman Spectra", Journal of Raman Spectroscopy (2002) pp. 580-585, vol. 33.

Dong, J. et al., "Metal Binding and Oxidation of Amyloid-B Within Isolated Senile Plaque Cores: Raman Microscopic Evidence", Biochemistry (2003), pp. 2768-2773, vol. 42.

Frank, C.J. et al., "Characterization of Human Breast Biopsy Specimens with Near-IR Raman Spectroscopy", Analytical Chemistry, (1994) pp. 319-326, vol. 66.

Haka, A.S., et al., "Identifying Microcalcifications in Benign and Malignant Breast Lesions by Probing Differences in their Chemical Composition Using Raman Spectroscopy", Cancer Research (2002) pp. 5375-5380, vol. 62.

Hanlon, E.B. et al., "Prospects for In Vivo Raman Spectroscopy", Phys. Med. Biol. (2000) pp. R1-R59, vol. 45.

Lakshmi, R.J. et al., "Tissue Raman Spectroscopy for the Study of Radiation Damage: Brain Inradiation of Mice", Radiation Research (2002) pp. 175-182, vol. 157.

Liu, C.H. et al., "Near-IR Fourier Transform Raman Spectroscopy of Normal and Atherosclerotic Human Aorta", Lasers in Life Science (1992) pp. 257-264, vol. 4.

Miura, T. et al., "Binding Mode of Congo Red to Alzheimer's Amyloid B-peptide Studied by UV Raman Spectroscopy", Journal of Raman Spectroscopy (2002) pp. 530-535, vol. 33.

Mizuno, A. et al., "Near Infrared FT-Raman Spectra of the Rat Brain Tissues", Neuroscience Letters (1992) pp. 47-52, vol. 141.

Mizuno, A. et al., "Near Infrared Fourier Transform Raman Spectroscopic Study of Human Brain—Tissues and Tumors", Journal of Raman Spectroscopy (1994) pp. 25-29, vol. 25.

Naumann, D., "FT-Infrared and FT-Raman Spectroscopy in Biomedical Research", Applied Spectroscopy Reviews (2001) pp. 239-289, vol. 36.

Petrick, W., "Mid-Infrared and Raman Spectroscopy for Medical Diagnostics", Applied Spectroscopy Reviews (2001) pp. 181-237, vol. 36.

Sajid, J. et al., "Fourier Transform Vibrational Spectroscopic Analysis of Human Cerebral Tissue", Journal of Raman Spectroscopy (1997) pp. 165-169, vol. 28.

Boppart, S.A. et al., "Optical Coherence Tomography for Neurosurgical Imgaing of Human Intracortical Melanoma", Neurosurgery (1998) pp. 834-841, vol. 43.

* cited by examiner

DYNAMIC IMAGING OF BIOLOGICAL CELLS AND OTHER SUBJECTS

BACKGROUND OF THE INVENTION

The invention relates generally to the fields of Raman spectroscopy and microscopic imaging of biological cells. The invention also relates to dynamic chemical imaging in general.

Understanding what is occurring, particularly on a molecular scale, in and among biological cells permits one to understand the behavior of the cells and influence their behavior in desired ways. For instance, most drugs exert their pharmacological effects based on their effects on cells. However, it has been difficult to understand the effects of a drug on an individual cell or small group of cells on a biochemically-relevant scale. Instead, macroscopic effects of a drug on a tissue or an entire organism have been observed and extensive experimentation and educated guessing has been required to understand the biochemical basis of a drug's effect. A significant need exists for methods of better observing the interactions of cells with each other and with the chemicals and phenomena (e.g., temperature or fluid shear stress) that occur in their environment. The present invention satisfies this need by providing a method of dynamically imaging chemical and biological systems on a scale relevant to understanding behavior and characteristics of individual cells and their subcellular components.

Jian Ling and colleagues have described a microscopic system for obtaining limited Raman spectral information from cells. See, for example Ling et al., 2002, Appl. Optics 41(28):6006-6017; U.S. Provisional Application 60/189,123, filed 14 Mar. 2000; U.S. Non-provisional application Ser. No. 09/804,774; and U.S. Non-provisional application Ser. No. 10/750,603. The Applied Optics manuscript describes a univariate method purportedly used to prepare images showing distribution of paclitaxel in breast cancer cells. The methods involve combining an optical image of a cell with a image of the cell prepared by subtracting combined Raman scattered and fluorescently-emitted radiation at 1080 $cm^{-1}$ (a Raman shift (RS) value at which scattering attributable to paclitaxel is purported to be insignificant) from combined Raman scattered and fluorescently-emitted radiation at 1000 $cm^{-1}$ (an RS value at which paclitaxel is purported to exhibit a peak).

It is unclear whether the data of Ling et al. support their contention that they are observing paclitaxel in breast cancer cells. For example, they obtain a Raman spectrum of paclitaxel in powdered form (FIG. 3 in the paper, FIG. 1 in the patent applications) and demonstrate that scattering at 1002 $cm^{-1}$ is much greater than scattering at 1080 $cm^{-1}$. A Raman spectrum of paclitaxel+ethanol+CREMAPHOR (RTM)+ PBS (FIG. 4 in the paper) purportedly shows that the paclitaxel Raman peak at 1002 $cm^{-1}$ is preserved (but shifted to 1000 $cm^{-1}$) in this mixture and that there is little or no RS for paclitaxel at 1080 $cm^{-1}$. The figure shows a small peak at 1000 $cm^{-1}$ and a possibly broad peak or shoulder at 1080 $cm^{-1}$, but there is no data from which to determine what, if any, contribution paclitaxel makes to the 1080 $cm^{-1}$ characteristic. The figure is also not corrected for fluorescent emission.

Even assuming that Ling et al. were able to identify paclitaxel in solution in FIG. 4 of the paper, it is not clear what the Raman spectrum of paclitaxel would look like when it is associated with a cell or a component of a cell, such as a microtubule. In short, it is not clear that the Raman signal that Ling et al. observe in paclitaxel-treated cells can, in fact, be correlated with the presence of paclitaxel.

Comparing the Raman images (center column in FIG. 8 of the Ling paper), it remains unclear what is being imaged, although at least some of whatever is being imaged is clearly shown (first row) to be present prior to treatment of the cells with paclitaxel. It is uncertain whether paclitaxel binding with microtubules would be expected to be as clumped as the Raman-active entities in the pictures in FIG. 8 appear to be. Microtubules are often substantially broadly spread throughout the cell, except during mitosis.

The univariate method of analyzing Raman scattering purportedly caused by paclitaxel may, even if it is valid under the circumstances purportedly present in the mixture studied by Ling et al. (i.e., a single strong Raman peak purportedly corresponding to paclitaxel and the particular deconvolution scheme), be limited in its utility to the particular conditions present in their experimental system. Such univariate analysis is unlikely to be broadly applicable. For instance, it is an inappropriate methodology to use for analysis of systems that exhibit more complex Raman spectra than that purportedly exhibited by the system described by Ling et al.

Another shortcoming of the optical systems used by Ling et al. is that it employs a rotating dielectric bandpass filter system to select Raman shift values for analysis. This system requires physical rotation to analyze different Raman shift values, preventing rapid analysis of multiple Raman shift values. Furthermore, rotation of the system displaces the image, requiring realignment of the Raman and optical images.

Sharonov et al. (1994, Analytica Chimica Acta 290:40-47) describe a cellular imaging system that relies on assessment of fluorescent emissions from cells and/or compounds in the cellular milieu. A significant drawback of imaging systems that rely on detection of fluorescence is that such systems exhibit relatively low spectral resolution, owing to the broad spectral width of most, if not all, fluorescent emissions. Another drawback is that many molecules and cellular components of interest do not fluoresce. Such molecules and components cannot be fluorescently imaged unless labeled—a process which can alter the behavior and characteristics of the molecule or component. Furthermore, live and dead cells often exhibit intense fluorescence background emissions that can interfere with fluorescent observation of a target of interest. Because most fluorescent emissions are not specific for the molecular species emitting the radiation, such background can complicate or prevent efforts to meaningfully interpret fluorescence.

U.S. Pat. No. 5,784,162 discloses methods of quantitatively detecting components in three dimensions in an environment containing cells or tissues. The patent discloses spectral imaging methods. The methods involve combining spectroscopic and imaging data. Spectral unmixing techniques are described in the context of fluorescence microscopy. The systems involve use of an optical path having a physically rotatable element for modulating optical interference. The system uses a stationary detector that is asserted to exhibit one-to-one correspondence with areas of the sample being imaged. This patent describe spectral imaging, rather than chemical imaging. Spectral imaging is low resolution and cannot spectrally resolve individual molecular species. The technology described in this patent is appropriate for analysis of large signals, such as fluorescent emissions, but is inappropriate for analysis of weaker signals, such as Raman scattered radiation.

U.S. Pat. No. 6,070,583 discloses methods of fluorescence and Raman imaging in two and three dimensions. The methods rely on temporally resolving inelastically scattered radiation assessed at multiple detection points surrounding an illuminated point to determine the distance of the scattering body from each of the detection points. Two- and three-dimensional representations of the illuminated system can be constructed from these data. The patent discloses that Raman spectral characteristics of scattered light can be used to characterize the chemical identity of the scattering body. The patent does not disclose whether the methods can be used to detect scattering bodies smaller than tissue lesions. Furthermore, the patent does not disclose combining spatial resolution data with optical imaging data, since the patent is directed to planar tomographic analysis of macroscopic tissues.

Chemical imaging is known in the art. One example of an apparatus used for chemical imaging is taught in U.S. Pat. No. 6,002,476, entitled "Chemical Imaging System," to Treado et al. Among other things, U.S. Pat. No. 6,002,476 teaches the use of Raman chemical imaging for analysis of a static sample, e.g., for assessing whether a particular tissue sample corresponds to normal tissue or breast cancer tissue. Other chemical imaging systems for assessment of static samples exist in the art.

In contrast to the prior art, the present invention uses chemical imaging to assess and observe non-static samples (i.e., samples that vary over time). Among other things, the present invention may be used to detect dynamic changes that occur in the sample over an observation period.

BRIEF SUMMARY OF THE INVENTION

The invention relates to a method of cellular imaging. The method comprises illuminating at least a portion of a cell with substantially monochromatic light and assessing Raman-shifted light scattered from the illuminated portion at a plurality of discrete times. The Raman-shifted light can be assessed at a plurality of Raman shift (RS) values at each of the discrete times, and the RS values can be selected to be characteristic of a first pre-selected component (e.g., a drug) at each of the discrete times. RS values characteristic of a second pre-selected component, such as a metabolite of a drug or a cellular constituent that is known to exhibit different Raman spectra before and after the cell is treated with a compound, can be followed.

The present invention is also directed to a system and method that can be used in performance of the methods described herein, regardless of whether the sample imaged contains cells (living, quiescent, or dead cells) or not. The system and method are useful for detecting dynamic changes that occur in a sample between a first time interval and a second time interval using a series of at least first and second sequential chemical images of the sample, wherein the first chemical image corresponds to an image of the sample during a first time interval, and the second chemical image corresponds to an image of the sample at a second time interval after the first time interval.

During the first time interval: (i) the sample is illuminated with a plurality of photons and photons are scattered or emitted by the sample; (ii) a two-dimensional array of detection elements is used to simultaneously detect scattered or emitted photons in a first predetermined wavelength band from different locations on or within the sample; and (iii) the two-dimensional array of detection elements is thereafter used one or more additional times to simultaneously detect scattered or emitted photons in one or more predetermined wavelength band(s) (which can be the same as or different from the first band) from different locations on or within the sample. The outputs of the two-dimensional array of detection elements during the first time interval are then combined to generate the first chemical image of the sample.

During the second time interval: (i) the sample is illuminated with a plurality of photons and photons are scattered or emitted by the sample; (ii) the two-dimensional array of detection elements is used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the second time interval are then combined to generate the second chemical image of the sample.

Dynamic changes occurring in the sample between the first time interval and the second time interval are detected based on one or more differences between the first and second chemical images.

The present invention permits rapid observation of the sample with full spatial information, and allows the monitoring of the evolution and changes in the sample that are naturally proceeding or occurring (i.e., under equilibrium conditions), as well as those that are additionally forced or imposed by creating a non-equilibrium condition via an external means (e.g., one or more external fields or forces applied to the sample). In certain embodiments, the external means may be applied to a specific location within the sample (rather than the whole sample).

DETAILED DESCRIPTION OF THE INVENTION

Figure 1:
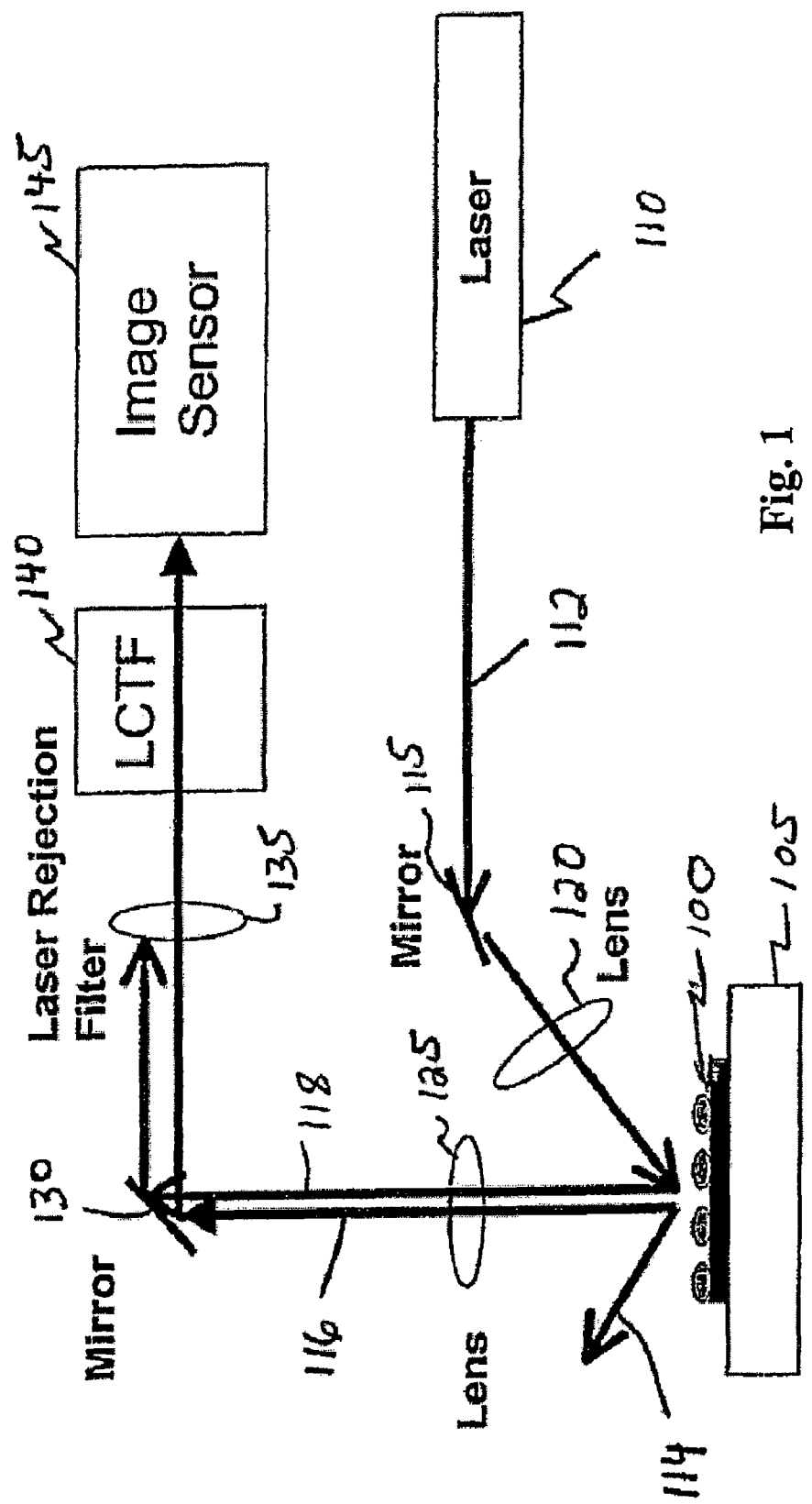
FIG. 1 schematically represents an apparatus according to one embodiment of the disclosure.

Raman spectroscopic analysis of chemical systems can yield information that reflects occurrence of particular chemical species present in the system. Raman chemical imaging can further indicate the physical location of the chemical species in the system, physical or chemical information (e.g., crystalline state of the species and information about the environment in which the species occurs), and information about the amount or concentration of the species in the system or at particular locations therein.

A drug (or any other compound having one or more distinguishable Raman spectral features) can be assessed in a chemical system that includes live or dead cells, subject to the ordinary limitations of Raman spectral analysis of a system (e.g., ability to illuminate relevant parts of the system and collect Raman scattered light from those parts). Because individual cells are typically not opaque at many wavelengths used to illuminate samples in Raman spectroscopy or at many wavelengths at which scattered radiation is emitted, it is usually possible to obtain Raman spectral data and chemical images from the entire volume of an individual cell (i.e., by assessing the volume of the cell at multiple focal planes within or including the volume). This provides a projection of all the chemical or drug over the area of the cell as it lays flat on the substrate used for Raman examination. Thus, it should be possible to detect a Raman active compound throughout the volume of an individual cell.

Raman spectral data can be obtained for an individual cell or throughout three-dimensional masses of cells, subject to the ordinary limitations of Raman spectral analysis. For a single cell, performing Raman chemical imaging repeatedly using different focusing depths within the cell provides planar sections of such projections of the Raman chemical image throughout the volume of the cell. These chemical sections show subtle variations which can be assembled and processed to obtain three dimensional images of the drugs in cells. Such volumetric imaging depends on accurately achieving clear and accurate chemical images of the drug for each 'chemical' section (i.e., each focal plane), which is essential for such full volumetric imaging. Thus obtaining accurate chemical images for a single layer, section or two-dimensional projection of the cell as it lies on a substrate is important for volumetric imaging.

The methods described herein are suitable for chemical imaging for cells of substantially any type, including one or more cells of any eukaryote or prokaryote (or even mixed samples of the two or more cell types). Suitable cells include, by way of examples, cells of humans, non-human animals, agriculturally significant plants (e.g., crop plants and weeds) or other plants, fungi, protists, eubacteria, archaebacteria, and mycoplasmas. Cells assessed using these methods can be obtained from a sample and imaged at a remote location, optionally after maintaining the cells in culture, treating the cells with a fixative, treating the cells with a drug, freezing the cells, or some combination of these. Alternatively, when the location of the cells and the design of the equipment described herein are compatible, the cells can be imaged in situ, for example in a human tissue, on the surface of an object, or within a three-dimensional body that permits Raman spectral analysis of at least a part of its interior.

A complication that affects Raman spectral analysis of most biological systems that include living cells (and other systems) is that living and dead cells commonly contain components that fluoresce intensely upon illumination with radiation used in Raman analysis. Because the spectral width of fluorescent emissions is generally much broader than the spectral width of individual Raman features and the intensity of fluorescent emissions is often greater than the intensity of Raman scattered radiation, it masks the Raman signals making it difficult to discern Raman and fluorescent radiation from a sample, and spectral processing techniques can be required to do so.

In order to separate the weak Raman signal from such background and other chemical signals in the cell, requires specialized techniques and analysis. Ling et al., in the Applied Optics manuscript mentioned herein, purport to use a single Raman peak of a drug to image its location in a cell, which is referred to as a univariate analysis. An alternate approach which we have found superior is to collect chemical images using multiple portions of the Raman spectrum for an analyte and use of many Raman peaks and the subtle Raman features of the analyte (e.g., drug) to determine its presence and location in the cellular environment. Methods of this type are referred to as a multi-variate analysis. A univariate analysis is more problematical in that one needs to separate a single peak from a relatively intense fluorescent background and determine spatially where this peak occurs. Use of multiple features of the Raman spectral signature, which corresponds to the multiple peaks and their relative intensities for the drug, permits much more effective distinction among Raman-scattering and fluorescing entities in a field of view, and thereby provides significantly higher ability to discriminate the drug from the background and other peaks that may occur. Use of a univariate approach requires many assumptions to deconvolute a single peak from not only the broad fluorescent background but also from other chemicals and Raman peaks in a system. Any changes in this single Raman peak of the drug common for chemical interactions in the cell becomes problematical.

Another very important point is that when a drug binds with a cell or a cellular component, some of the vibrations detected by Raman within the drug compound will often shift, which reflects the type of interactions and bonding of the drug within the cell. Being able to detect these shifts independent of the mode of imaging is critical to using these Raman peak values for further detailed information regarding drugs in cells. Use of a single filter at one wavelength precludes such important changes from being observed or imaged.

A Cellular-Scale Raman Imaging System

In the context of this application, the Raman imaging system (RIS) can be basically any Raman microscope equipped with the apparatus needed to perform the analysis described herein. By way of example, the RIS can be substantially any of the systems described in U.S. Pat. No. 6,002,476 of Treado, the FALCON™ device of ChemImage, or a similar device. Another appropriate device and system are described herein.

For analysis of an analyte within a cell, the device should be equipped with magnification optics that permit visualization of cells or subcellular structures, depending on the degree of detail needed in the analysis (i.e., the size of the target or the desired resolution of portions of the target). A frame of Raman spectral data is obtained for a desired target (e.g., a cell or a portion of a cell) at one or more Raman shift (RS) values that are characteristic of an analyte. By way of example, the analyte can be a Raman-active drug molecule or a Raman-active molecule of cellular origin that is known or expected to be influenced by a drug molecule. Occurrence, approximate concentration or amount, and location of the Raman-active component can be assessed in the focal plane of the field of view. The Raman spectral data can be combined with (e.g., overlaid with) a frame of image data obtained by another spectroscopic method, such as visible light reflectance microscopy. The other spectroscopic method can (and preferably does) use the same optical path as Raman spectral analysis, or the same portion of the optical path (through the sample) used for collection of Raman-scattered light (even if separate detectors are used to assess Raman-scattered and other radiation).

Once a frame of Raman spectral data is obtained, a second frame of Raman spectral data can be obtained at a later point in time, the interval between the two frames being not less than the time it takes to acquire Raman spectral (and optionally other spectral) data from the target and to record it. The time between frames can be longer than that period, if desired. For example, in a system in which changes in Raman-active targets are perceptible only on a time scale of not less than seconds, there may be little advantage in acquiring many frames of Raman spectral data per second. Thus, the time frame necessary for data acquisition can determine which biological or biochemical systems are appropriate for analysis with a particular RIS. For instance, an RIS may be inappropriate for assessment of processes in which the time scale of changes desired to be observed is significantly (e.g., orders of magnitude) faster than the rate of data acquisition of the RIS.

Because the RIS's described herein can collect Raman spectral data over an entire field of view very quickly, it can capture meaningful data for processes having a characteristic time on the order of milliseconds, tens of milliseconds, hundreds of milliseconds, or longer. Few drugs appear to exert their physiological effects on cells in time periods shorter than this. Thus, the RIS's described herein are suitable for collecting Raman spectral information about the cellular and sub-cellular location of Raman-active components, such as drugs and their metabolites. Because this information can be collected rapidly in a succession of data frames and those data frames can be stored and replayed, the method is useful for examination of processes in which changes occur in Raman-active components over time. These RIS's overcome drawbacks of systems such as those of Ling et al. because they does not require manipulation of moving parts and are capable of obtaining Raman spectral data at multiple RS values in a time frame suitable for analysis of high-speed processes. Thus, using the Ling et al. paper as an example, an RIS of the type described herein is able to gather a broader range of Raman spectral data corresponding to paclitaxel in each frame, permitting greater distinction between paclitaxel and other cellular components which happen to exhibit Raman scattering at 1000 $cm^{-1}$ (e.g., see the pre-paclitaxel-treated cell controls in Ling's paper).

The dynamic chemical imaging methods described herein can be used in conjunction with the Raman imaging strategies disclosed in other ChemImage patent documents, such as the United States provisional patent applications filed on 30 Jun. 2004 (Ser. Nos. 60/584,719 and 60/584,718) for multimodal and multipoint analytical systems. The spectral unmixing and fluorescence-correction methods described in those other applications are equally applicable to the dynamic chemical imaging methods described herein.

An example of a process for which the dynamic chemical imaging methods described herein can be used is assessing motion of Raman-active particles (e.g., cells of a particular type or polymer spheres) in an environment that can include Raman-distinguishable liquids, gases, or other particles (e.g., cells of one or more other types or spheres of other polymer types). The dynamic chemical imaging methods can also be used to assess processes in which the shape, size, or Raman characteristics of a target change over the course of multiple frames of data acquisition. By way of example, such methods can be used to assess growth of crystals, change of particles or regions of molecules from one Raman-active form to another or to a Raman-inactive form (or vice versa).

The dynamic chemical imaging methods can be used to follow individual Raman-active particles having a size approaching the limit of resolution of the optical systems used, at the wavelength(s) used for assessing the particles. Even in systems in which individual Raman-active particles cannot be distinguished from one another, the Raman spectral characteristics of an area that includes such particles can indicate what is happening to those particles, at least on an averaged basis. In this way, the behavior of Raman-active virus particles can be observed, for example.

In addition to acquiring Raman spectral data in a focal plane over time, a fourth dimension of analysis can be obtained by assessing multiple adjacent or spaced focal planes (e.g., corresponding to multiple parallel adjacent 'slices' through a sample, to multiple parallel regularly-spaced 'slices,' or to multiple non-parallel focal planes). The time required to obtain Raman spectral data for each of the multiple focal planes can limit the acquisition rate for data corresponding to the entire sample. In this way, for example, occurrence, location, and approximate concentration or amount of a Raman-active drug (or another Raman-active substance) in a cell can be assessed in three-dimensions by repeatedly assessing Raman scattering from multiple stacked 'slices' of the volume containing the cell.

The speed of Raman data acquisition is limited largely by the amount of Raman scattered radiation, which is ordinarily small. An important part of a Raman scattering detection system is that it is sensitive to polarization. That is, the system can be configured so that it detects only scattered light having one or more particular polarizations. Because the Raman scattered light scattered by a sample is not polarized in a single direction (it includes photons exhibiting all polarizations), about half the light intensity can be lost at the stage of detection. One way to increase data acquisition speed is to detect light in multiple polarization directions (e.g., speed could be doubled by detecting scattered light having orthogonal polarizations). This can be achieved with two CCD cameras, for example, each of which detects an independent channel of polarization. The two camera can operate simultaneously, but in a chronologically staggered fashion, such that one begins its data collection cycle when the other is part-way (e.g., approximately half-way) through its data collection cycle. Furthermore, because Raman-shifted light scattered by ordered cells (e.g., cells aligned in a defined way in a tissue such as a membrane, a muscle, or a neuronal tissue) can exhibit significantly anisotropic polarization, assessment of scattered light having different directions or degrees of polarization can also yield useful information about the cells. An example of optical components that can be readily adapted for analysis of anisotropic polarization of Raman scattered light is described in Tsuboi 2002, J. Biomed. Opt. 7(3):435-441. Furthermore, because cells, drugs, subcellular components, substrates, and other components present in a microscopic field of view can exhibit anisotropic polarization, the ability of the RIS system to distinguish between such polarization can increase the information derivable from Raman analysis of a field of view.

Some of the advantages of using Raman chemical imaging devices described herein (such as the FALCON™ system of ChemImage) are as follows.

Because a solid-state detector is used (i.e., no moving parts) RIS can rapidly assess the intensity of scattered radiation at multiple wavelengths and with high spatial resolution (i.e., can rapidly switch between RS values without manipulating moving parts), the RIS obtains such data over an entire field of view at one time (i.e., in parallel) which includes the entire cell or cells at any arbitrary magnification, the RIS can be used to collect Raman spectral information from cells and sub-cellular regions, and the information that is collected can be used to i) correct for background fluorescence and ii) identify chemical species in the viewing field of analysis with high specificity. Unlike the system described by Ling et al., the RIS described herein can gather Raman spectral information at multiple RS values, permitting better differentiation among chemical species having similar structures and permitting better correction for fluorescent background. Commercial software packages, such as Chemimage Corporation's proprietary software CHEMIMAGE EXPERT™, can be used to perform multivariate analysis of the Raman-active species for as many as each of the pixels in the field of view. The speed of the RIS described herein also permits Raman spectral scanning of cells and cellular regions on a time scale practical for analysis of cellular composition.

Using the ChemImage FALCON™ instrument, for example, a Raman image at a single RS value can be acquired in as little as one second. For better spatial resolution, more time is preferable. For example, 10 to 30 seconds a frame, or even 60 seconds per frame, yields spatial resolution that is suitable for analysis of cells. There is a tradeoff one can make between time and resolution (both spatial and spectral). The exact parameters used depend on the equipment used and the spatial and spectral resolution required. Improvements in equipment components will increase the rate at which data can be acquired. For example, suitable cameras can currently collect Raman scattering information at a single RS value at the rate of about 50 milliseconds per frame. Improvements in other system components may eventually allow data acquisition rates approaching this speed. Data acquisition rates also depend on the complexity of the system being imaged. By way of example, there have been instances in which localized, endogenous molecules could be Raman imaged at a rate of 0.1 seconds per frame. Examples would include carbonaceous materials in rocks (diamond-like carbon in meteorites), carbonates in inorganic matrices, phosphates (calcifications) in tissues, and pharmaceutical compounds at high concentration in excipients.

The speed at which data can be acquired in three dimensions depends on both the data acquisition rate for single frames and the time required to shift the focal plane of the instrument used. For instance, it is possible using equipment described herein to take a single RS image of a cell in three dimensions (by changing the distance between the cell and the microscope objective) with an acquisition time of 2 seconds per frame. Moving the focal plane over 13 positions in the z direction permitted a total acquisition time of about 30 seconds (including some time for frame readout). In some embodiments, as many as 180 frames of data have been obtained for a single imaged volume in about half an hour. This is likely a greater amount of data than necessary to image the volume, but exemplifies some of the capacities of the systems described herein. Because the characteristic time (i.e., the period during which changes in the system can be related to one another in a meaningful way) of processes in cellular systems vary (some having characteristic times on the order of seconds, others on the order of hours, days, or longer), the requirements of a particular RIS system depend on the cellular characteristics being observed.

The speed of the RIS described herein permits Raman chemical imaging of targets that are moving at a much greater rate of speed than was possible with slower RIS's. Thus, movement of discrete particles can be analyzed, even if those discrete particles are mixed with other Raman-distinct particles. For instance, movement of a Raman-active agent within a cell can be followed in near-real time.

Because the RIS described herein can be used to assess other spectral features of a target (e.g., optical microscopic morphology, fluorescent emissions, etc.), the Raman data and other spectral data can easily be combined to present the combined information in a variety of informative ways. By way of example, Raman data indicating occurrence of a Raman-active agent at particular locations in a field of view can be combined with a visible microscopic image of cells in the field to indicate the location and amounts (relative or absolute) of the agent in various parts of the cell. Furthermore, because the RIS can assess Raman data at multiple RS values nearly simultaneously, conversion of one Raman-active agent to another (e.g., conversion of a drug to a metabolite of the drug) can be assessed in near real-time. The RIS's described herein are capable of rapid and extensive data acquisition, which permits multivariate analysis.

Although the methods can be practiced as described above, the following items are some ways of improving performance of the system.

The rapidity with which "frames" of Raman chemical image (RCI) data can be obtained determines the response rate of the system. Anything that decreases the time required to obtain a frame of data will increase the response rate (i.e., number of frames per unit of time) of the system. Thus, shortening either or both of the response time of the measurement system or the rate at which Raman data (or other data corresponding to the frame, if the other data are limiting the data acquisition rate) are acquired will improve the response rate of the system. The greater the number of RS values at which RCI data are collected, the longer will be the time required for Raman data acquisition. Thus, selecting RS values that correspond specifically to the target of interest (e.g., a drug) and which do not correspond to the environment in which the target is being imaged (e.g., other cellular constituents) can decrease the number of RS values at which data must be collected and improve the response rate. Similarly, shortening the period that Raman scattered radiation is collected by the detector will improve the response rate (at least up to the point at which the signal can be differentiated from noise).

Background noise can be obtained by illuminating the target along an axis different from the axis along which Raman-scattered light is collected.

The intensity of Raman-scattered light can be enhanced by a number of methods. For example, illuminating a target with light having a shorter wavelength will yield more intense Raman scattered light than light scattered by a target illuminated with light of a longer wavelength. However, shorter wavelengths of light produce more fluorescence backgrounds which mask or swamp other inelastic signals from the sample such as Raman. Furthermore, use of Raman-enhancing substrates to support the target (e.g., colloidal silver or gold substrates, as well as other known Raman-enhancing surfaces) can improve the intensity of the Raman signal. Cells can be cultured on such substrates, for example, or deposited onto substrates which include such materials.

As with any optical system, signal strength can be improved by reducing optical losses and enhancing detector sensitivity—thus, the RIS described herein can be used with substantially any Raman-compatible optical systems and detectors that exist currently or are hereafter developed. Employing multivariate statistical image analysis ("chemometrics") will increase the sensitivity of the ChemImage RIS technology. Preferred embodiments include the use of one or more of i) correlation analysis to improve drug target signal to noise (SNR) ratio within an image pixel; ii) principal components analysis (PCA) as a noise reduction technique; and iii) evolving factor analysis as a means to detect dynamic changes in the Raman spectrum.

The Chemical Imaging Standard Addition Method (described in ChemImage's U.S. Pat. No. 6,734,962, relating to NIR microscopy), can be employed as a means to locate and semi-quantitatively estimate drug in cell concentration.

Radiometric SNR detector performance models can be employed to estimate the concentration of a drug within a cell, without the use of internal calibration standards.

System and Method for Dynamic Chemical Imaging

The methods described in this section can be performed using a system or method for detecting dynamic changes that occur in a sample between a first time interval and a second time interval using a series of at least first and second sequential chemical images of the sample. The first chemical image corresponds to an image of the sample during a first time interval. The second chemical image corresponds to an image of the sample at a second time interval after the first time interval.

During the first time interval: (i) the sample is illuminated with a plurality of photons to thereby produce photons scattered or emitted by the sample; (ii) a two-dimensional array of detection elements is then used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the first time interval are then combined to generate the first chemical image of the sample.

During the second time interval: (i) the sample is illuminated with a plurality of photons to thereby produce photons scattered or emitted by the sample; (ii) the two-dimensional array of detection elements is then used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the second time interval are then combined to generate the second chemical image of the sample.

Dynamic changes occurring in the sample between the first time interval and the second time interval are detected based on one or more differences between the first and second chemical images.

The present invention permits rapid observation of the sample with full spatial information, and allows the monitoring of the evolution and changes in the sample that are naturally proceeding or occurring (i.e., under equilibrium conditions,) as well as those that are additionally forced or imposed by creating a non-equilibrium condition via an external means (e.g., one or more external fields or forces applied to the sample). In certain embodiments, the external means may be applied to a specific location within the sample (rather than to the whole sample).

FIG. 1 schematically represents an apparatus according to one embodiment of the disclosure. The apparatus shown in FIG. 1 enables providing a high optical throughput for imaging low light levels at variable magnification. Referring to FIG. 1, sample 100 is positioned on substrate 105. Substrate 105 can be any conventional microscopic slide or other means for receiving and optionally securing sample 100. Light source 110 is positioned to provide incident light to sample 100. Light source 110 can include any conventional photon source, including laser, LED, and other IR or near IR devices. Light source 110 may also be selected to provide evanescence illumination of the sample. In one embodiment, the bandwidth of the source is in the range of about 15-25 $cm^{-1}$.

Referring still to FIG. 1, it should be noted that light source 110 is positioned to provide incident light at an angle with respect to sample 100, as opposed to light shining orthogonal to sample 100. In other words, the radiation used to illuminate the sample need not pass through the optical train of a conventional microscope (or macroscope); rather, it can illuminate the sample at an oblique angle from above or below sample 100. Photon beam 112 is received and deflected by mirror 115 through lens 120. Lens 120 may optionally be used to focus the light on sample 100. Alternatively, the photon beam 112 may be directed towards the sample 100 without the need for the mirror 115.

The multitude of photons in beam 112 reaching sample 100 illuminate the sample and are either scattered or absorbed by the sample, which can result in subsequent emission (luminescence) at different wavelengths. As known to those skilled in the art, the term "luminescence" includes a wide range of optical processes described using other names. These include: fluorescence, phosphorescence, photoluminescence, electroluminescence, chemiluminescence, sonoluminescence, thermoluminescence and even up-conversion. Scattered photons are schematically represented as beams 116 and 118 while specularly reflected photons are represented schematically as beam 114. Luminescently-emitted photons are also represented as beam 118. Optical lens 125 is positioned to receive photon beams 116 and 118. Optical lens 125 may be used for gathering and focusing received photon beams. This includes gathering and focusing both polarized and non-polarized photons. In general, the sample size determines the choice of light gathering optical lens 125. For example, a microscope lens may be employed for analysis of the sub-micron to micrometer specimens. For larger samples, macro lenses can be used. Optical lens 125 (as well as lens 120) may include a simple reduced resolution/aberration lens with a larger numerical aperture to thereby increase system's optical throughput and efficiency. Mirror 130 is positioned to direct emitted or scattered photon beams 118 to tunable filter 140. It should be noted that placement of mirror 130 is optional and may be unnecessary in configurations where tunable filter is positioned above sample 100.

Laser rejection filter 135 may be positioned prior to tunable filter 140 to filter out scattered illumination light represented by beam 116 and to optimize the performance of the system. In other words, rejection filter 135 enables spectrally filtering of the photons at the illuminating wavelength.

A conventional tunable filter (including electro-optical, mechanical or other tunable filters) can be used to further the principles of the disclosure. Examples of suitable tunable filters include a liquid crystal tunable filter ("LCTF") or an acousto-optical tunable filter ("AOTF") can be used to further the principles of the disclosure. The electro-optical filters (or other tunable filters) allow specific wavelengths or ranges of wavelengths of light to pass through as an image, depending on the control signals placed on the device by a controller (not shown in FIG. 1). The wavelengths that can be passed through tunable filter 140 may range from 200 nanometers (ultraviolet) to 2000 nanometers (i.e., the far infrared). The choice of wavelength depends on the desired optical region and/or the nature of the sample being analyzed.

Image sensor 145 may be a digital device such as for example a two-dimensional, image focal plane array ("FPA") or CCD or CMOS sensor. The optical region employed to characterize the sample of interest governs the choice of FPA detector. For example, a two-dimensional array of silicon charge-coupled device ("CCD") detection elements, can be employed with visible wavelength fluorescence and Raman spectroscopic, while gallium arsenide (GaAs) and gallium indium arsenide (GaInAs) FPA detectors can be employed for image analyses at near infrared wavelengths. The choice of such devices depends on the type of sample being analyzed. In one embodiment, each detection element in the two-dimensional array of detection elements used to form image sensor 145 functions to detect photons scattered or emitted from a different spatial location on or within the sample. In one embodiment, image sensor 145 produces digital images of the entire view of the sample as processed by tunable filter 140.

Figure 2:
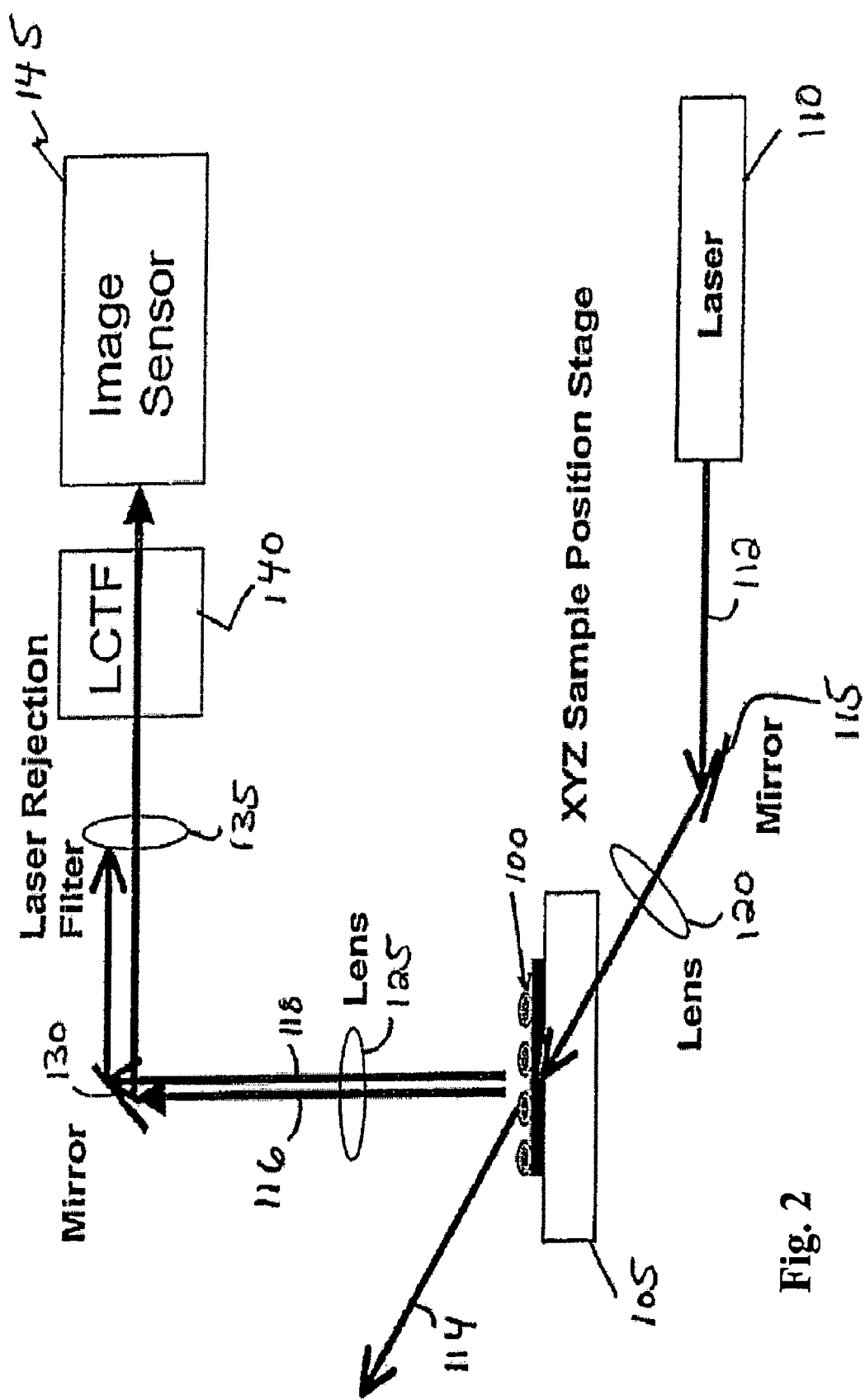
FIG. 2 schematically represent an apparatus according to another embodiment of the disclosure.

FIG. 2 schematically represents an apparatus according to another embodiment of the disclosure. More specifically, FIG. 2 schematically shows a high optical throughput configuration for imaging low light levels at variable magnification. The collection of optics are similar to that illustrated in FIG. 1 but with illumination from the underside of sample 100.

It is noted that in both FIGS. 1 and 2, sample 100 is illuminated at an oblique angle relative to beams 116 and 118. Specifically referring to FIG. 2, photonic beam 120 and the plane axis of sample 100 define an oblique angle. It has been found that through oblique illumination, a so-called "Dark Field Raman Imaging" is developed. As opposed to the conventional bright field Raman configuration, the dark field Raman imaging decouples the image capture optics from the delivery of exciting radiation. Consequently, internal scattering and attenuation of the incident radiation has been minimized to improve the signal-to-noise (S/N) ratio. Also, the location of the optical source external to the optical train further allows the use of a lower cost, less powerful illumination source as well as enables a simpler, less expensive integration of several illumination sources into the system. The application of this configuration is not limited to Raman and luminescence imaging and can be successfully used, for example, with conventional spectroscopy.

In each of the embodiments shown in FIGS. 1 and 2, a computer or processor (not shown in the figures) can be coupled to and used to control the optical devices including light source (110), lenses (120, 125, 135), mirrors (115, 130) and tunable filter (140). The computer can also be coupled to image sensor 145 and functions to generate "chemical images" from the output of the image sensor 145. In one embodiment, each chemical image is a spatially accurate wavelength-resolved image of the sample that is formed from multiple "frames"; wherein each frame has plural spatial dimensions and is created from photons of a particular wavelength (or wave number) or from photons in a particular wavelength band (or wave number band) that are collected simultaneously by image sensor 145 from different spatial locations on or within sample 100. In each chemical image, multiple frames may be combined to form a complete image across all wavelengths (wave numbers) of interest. The chemical images generated by the computer may be further analyzed by the computer and/or displayed to a user.

The present invention uses an apparatus such as those shown in FIGS. 1 and 2 to detect dynamic changes that occur in sample 100 between a first time interval and a second subsequent time interval using a series of at least first and second sequential chemical images of sample 100. During the first time interval: (i) sample 100 is illuminated with photons from source 110 to thereby produce photons scattered or emitted by sample 100; (ii) image sensor 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), image sensor 145 is thereafter used to simultaneously detect scattered or emitted photons from different locations on or within the sample. The outputs of detector 145 (for each of the wavelengths or wavelength bands selected by tunable filter 140 during the first time interval) are then combined by the computer (not shown in the figures) to generate the first chemical image of the sample.

During the second subsequent time interval: (i) sample 100 is illuminated with photons from source 110 to thereby produce photons scattered or emitted by sample 100; (ii) image sensor 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), image sensor 145 is thereafter used to simultaneously detect scattered or emitted photons from different locations on or within the sample. The outputs of detector 145 (for each of the wavelengths or wavelength bands selected by tunable filter 140 during the first time interval) are then combined by the computer to generate the second chemical image of the sample.

Dynamic changes occurring in the sample between the first time interval and the second time interval are detected based on one or more differences between the first and second chemical images. Computer analysis of the chemical image with or without the physical image may be used to detect (or enhance detection of) the dynamic changes. The dynamic changes may also be detected by a user viewing a display of the chemical images.

In various embodiments, a series of many sequential chemical images are obtained rapidly in succession to generate a "movie" of the sample. For example, as many as 100 chemical images per second of the sample may be obtained in order to detect dynamic changes in the sample in substantially real-time. In some embodiments, the temporal resolution of the chemical images in the sequence may be as fine a 1 millisecond, i.e., the system will generate a chemical image of the sample every millisecond. Other temporal resolutions can also be selected including, for example, a temporal resolution that equates to chemical images spaced apart by as much as 15 minutes between adjacent images. When using the present invention to monitor a particular process or reaction, the temporal resolution selected should be sufficient to detect dynamic changes of interest that occur in the sample over time.

The present invention thus permits rapid observation of sample 100 with full spatial information, and allows the monitoring of the evolution and changes in sample 100 that are naturally proceeding or occurring (i.e., under equilibrium conditions), as well as those that are additionally forced or imposed by creating a non-equilibrium condition via an external means (e.g., one or more external fields or forces applied to the sample). In certain embodiments, the external means are applied to a specific location within sample 100 (rather than to the whole sample). Examples of samples that can be analyzed and observed used the dynamic chemical imaging techniques of the present invention includes biological samples or micro-fluidic circuits undergoing changes over time. These changes may include displacement, chemical interaction, a change in chemical state, phase change, growth, shrinkage, chemical decomposition, chemical metabolism, and physical strain. Numerous other examples of samples/changes applicable to the present invention will be recognized by the those skilled in the art and are considered within the scope of the present invention.

As noted above, the present invention may be used to detect dynamic changes in the sample that result from application of an external condition to the sample. Such external conditions include, for example, varying an electric or magnetic field applied to or within sample 100 between the first and second time intervals; varying an external optical field applied to or within the sample between the first and second time intervals, wherein the external optical field is distinct from the optical field initially used to illuminate the sample; varying the optical field applied to or within the sample between the first and second time intervals, wherein the additional optical field is produced by pulsing the optical filed used to illuminate the sample; varying internally generated photons applied to or within the sample between the first and second time intervals; varying a polarization used to illuminate the sample between the first and second time intervals; varying a temperature of the sample between the first and second time intervals; varying a pressure applied to the sample between the first and second time intervals; or varying a stress applied to or within the sample between the first and second time intervals. In other embodiments, a chemical gradient associated with the sample (e.g., a chemical gradient imposed on the sample) varies between the first and second time intervals. In still further embodiments, a physiological or biological stress is induced in the sample between the first and second time intervals. In another important embodiment, the dynamic effect of adding one or more chemical species (e.g., a pharmaceutically active agent, an antibody, or a nucleic acid) to a sample is observed at multiple times. As disclosed herein, such a sample can be prepared from or include living cells.

In some embodiments, each chemical image in the sequence is made up of multiple separate spatially accurate wavelength-resolved images of the sample (each of which is formed from multiple "frames" as discussed above), wherein each of the multiple separate spatially accurate wavelength-resolved images corresponds to one of a plurality of different depths within the sample. These embodiments are useful for detecting chemical changes occurring throughout the volume of sample 100, rather than changes occurring on a single surface or plane of the sample.

In still further embodiments, differences between or among various chemical images in the sequence can be correlated (using, e.g., the computer discussed above or by a user) with orthogonal (i.e., complementary) measurements of the sample made during each of the time intervals associated with the sequence, in order to enhance detection or observation of dynamic changes in the sample. Examples of orthogonal measurements that may be used include measurements made using the following modalities: Raman scattering, near infrared absorption (NIR), visual imagery, video or luminescence. Other orthogonal measurements may also be used and are considered to be within the scope of the present invention.

Definitions

As used herein, each of the following terms has the meaning associated with it in this section.

"Bandwidth" means the range of wavelengths in a beam of radiation, as assessed using the full width at half maximum method.

"Bandpass" of a detector or other system means the range of wavelengths that the detector or system can distinguish, as assessed using the full width at half maximum intensity method.

The "full width at half maximum" ("FWHM") method is a way of characterizing radiation including a range of wavelengths by identifying the range of contiguous wavelengths that over which the magnitude of a property (e.g., intensity or detection capacity) is equal to at least half the maximum magnitude of that property in the radiation at a single wavelength.

"Spectral resolution" means the ability of a radiation detection system to resolve two spectral peaks.

Although the terms "optical" and "spectroscopic" are used herein to refer to properties of materials (and to methods of assessing such properties), the two terms are understood to refer to the interaction of electromagnetic radiation, electrons, or neutrons with the materials. For example, although electron microscopy is not always commonly considered a "spectroscopic" or "optical" method, the two terms are used inclusively herein to encompass electron microscopy.

EXAMPLE

The invention is now described with reference to the following Example. This Example is provided for the purpose of illustration only, and the invention is not limited to this Example, but rather encompasses all variations which are evident as a result of the teaching provided herein.

Raman chemical imaging of a Raman-active compound in a breast cancer cell.

A Raman-active compound was contacted with a breast cancer cell. Subsequent Raman chemical imaging of the cell was performed. Raman spectra obtained from the cell prior to and after contacting it with the compound indicated significant differences in Raman spectral features at about 900 cm$^{-1}$ and at about 2250 cm$^{-1}$. Raman chemical imaging of the cell after contacting it with the compound demonstrated the location of the compound exhibiting the 2250 cm$^{-1}$ feature in the cell cytoplasm.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of cellular imaging to assess an effect of a drug on a cell, the method comprising:
    (a) illuminating at least a portion of a cell with substantially monochromatic photons;
    (b) detecting Raman-shifted photons scattered from the illuminated portion to thereby form an image corresponding to Raman-shifted photons collected substantially simultaneously from a plurality of different spatial locations of the cell;
    (c) at each of the plurality of different spatial locations of the cell represented by the image, assessing the Raman-shifted photons at a plurality of Raman shift (RS) values characteristic of a pre-selected drug to thereby determine a first state of the cell;
    (d) after a time period following a first iteration of steps (a)-(c), repeating steps (a)-(c) to thereby determine a second state of the cell; and
    (e) comparing the first and second state of the cell to thereby assess an effect of the drug on the cell over the time period.

2. The method of claim 1 further comprising:
    (f) assessing the Raman-shifted photons at a plurality of Raman shift (RS) values characteristic of a pre-selected component wherein said pre-selected component is selected from the group consisting of: a metabolite of a drug, a cellular constituent, and combinations thereof.

3. The method of claim 1 wherein said cell is a living cell.

4. The method of claim 1 wherein said cell is a quiescent cell.

5. The method of claim 1 wherein said cell is a dead cell.

6. The method of claim 2 wherein said cellular constituent is selected from the group consisting of: a particular protein, an organelle, a protein complex, a compartment, a membrane, and combinations thereof.

7. A method of cellular imaging to assess an effect of a drug on a cell, the method comprising:
    (a) illuminating at least a portion of a cell with substantially monochromatic photons;
    (b) filtering Raman-shifted photons scattered from the illuminated portion to thereby form a filtered image;
    (c) collecting a first plurality of filtered images of the illuminated portion, wherein each filtered image corresponds to a different wavelength range of photons passed by the filter, and each filtered image corresponds to Raman-shifted photons collected substantially simultaneously from a plurality of different spatial locations of the cell;

(d) after a time period following a first iteration of steps (a)-(c), repeating steps (a)-(c) to collect a second plurality of filtered images; and (e) comparing the first and second plurality of filtered images to thereby assess an effect of the drug on the cell over the time period.

8. The method of claim 7 further comprising:

(f) assessing the Raman-shifted photons at a plurality of Raman shift (RS) values characteristic of a pro-selected component wherein said pro-selected component is selected from the group consisting of: a metabolite of a drug, a cellular constituent, and combinations thereof.

9. The method of claim 7 wherein said cell is a living cell.

10. The method of claim 7 wherein said cell is a quiescent cell.

11. The method of claim 7 wherein said cell is a dead cell.

12. The method of claim 8, wherein said cellular constituent is selected from the group consisting of: a particular protein, an organelle, a protein complex, a compartment, a membrane, and combinations thereof.

13. The method of claim 7 wherein said Raman-shifted photons arc filtered using a filter selected from the group consisting of: a tunable filter, a liquid crystal tunable filter. an acousto-optical tunable filter, an electro-optical tunable filter, and a mechanical tunable filter.

* * * * *